United States Patent [19]

Scrivens et al.

[11] Patent Number: 6,080,892
[45] Date of Patent: Jun. 27, 2000

[54] METHOD OF PRODUCING SUBSTITUTED BENZALDEHYDES WITH CATALYTIC AMOUNTS OF ACID

[75] Inventors: Walter A. Scrivens, Newberry; John G. Lever, Spatanburg, both of S.C.

[73] Assignee: Milliken & Company, Spartanburg, S.C.

[21] Appl. No.: 09/268,468

[22] Filed: Mar. 16, 1999

[51] Int. Cl.[7] .................................................. C07C 45/49
[52] U.S. Cl. ............................................ 568/428; 568/437
[58] Field of Search ...................................... 568/428, 437

[56] References Cited

U.S. PATENT DOCUMENTS

| | | | |
|---|---|---|---|
| 1,776,154 | 9/1930 | Knorr et al. . | |
| 1,935,914 | 11/1933 | Olson | 260/136 |
| 1,939,005 | 12/1933 | Guthke | 260/136 |
| 1,989,700 | 2/1935 | Larson | 260/136 |
| 2,053,233 | 9/1936 | Woodhouse | 260/116 |
| 2,158,518 | 5/1939 | Meuly | 260/599 |
| 2,158,519 | 5/1939 | Meuly | 260/599 |
| 2,271,299 | 1/1942 | Ipatieff et al. | 252/251 |
| 2,311,232 | 2/1943 | Ipatieff et al. | 252/251 |
| 3,369,048 | 2/1968 | Hamilton et al. | 260/599 |
| 4,195,040 | 3/1980 | Renner | 260/599 |
| 4,554,383 | 11/1985 | Knifton | 568/428 |
| 4,622,429 | 11/1986 | Blank et al. | 568/428 |
| 5,457,239 | 10/1995 | Frank et al. | 568/433 |
| 5,679,867 | 10/1997 | Bruce et al. | 568/428 |

OTHER PUBLICATIONS

Doko, Yoshiji et al., "Formylation of Methylnaphthalene Compounds with CO in HF–BF$_3$ Medium", *Sekiyu Gakkaishi*, 40, (2), pp. 115–123 (1997).

*Primary Examiner*—Sreeni Padmanabhan
*Attorney, Agent, or Firm*—Terry T. Moyer; William S. Parks

[57] ABSTRACT

This invention relates to a process for preparing specific substituted benzaldehydes through the reaction of substituted benzenes with carbon monoxide and aluminum chloride at a relatively low pressure, at a low temperature, and in the presence of at most a catalytic amount of acid (preferably aqueous HCl) and a solvent. The resultant substituted benzaldehydes are useful as precursors to the formation of a number of different compounds, such as dyestuffs, flavorings, fragrances, nucleating agents, polymer additives, and the like. The inventive method provides a very cost-effective and safe procedure for producing such substituted benzaldehydes at very high yields.

15 Claims, No Drawings

METHOD OF PRODUCING SUBSTITUTED BENZALDEHYDES WITH CATALYTIC AMOUNTS OF ACID

FIELD OF THE INVENTION

This invention relates to a process for preparing specific substituted benzaldehydes through the reaction of substituted benzenes with carbon monoxide and aluminum chloride at a relatively low pressure, at a low temperature, and in the presence of at most a catalytic amount of acid (preferably aqueous HCl) and a solvent. The resultant substituted benzaldehydes are useful as precursors to the formation of a number of different compounds, such as dyestuffs, flavorings, fragrances, nucleating agents, polymer additives, and the like. The inventive method provides a very cost-effective and safe procedure for producing such substituted benzaldehydes at very high yields.

BACKGROUND OF THE PRIOR ART

All U.S. Patent documents and other publication discussed below are herein entirely incorporated by reference.

Techniques for producing substituted benzaldehydes have been practiced for over a century. The primary method followed to formylate substituted benzene was the Gattermann-Koch reaction, developed in 1897. This reaction required the combination of equivalent amounts of aluminum chloride, carbon monoxide, and gaseous hydrogen chloride reacted in the presence of a substituted benzene. The temperature was controlled from 25 to 50° C., and the pressure was kept at 1,000 psig. Such a reaction yielded about 70% of the desired substituted benzaldehyde; however, the utilization of stoichiometric amounts of HCl (even in its gaseous state) and the need for high reaction pressures are highly undesirable from a safety standpoint.

Modifications of the Gattermann-Koch reaction have been developed for specific monoalkyl-substituted benzaldehydes, such as in U.S. Pat. No. 4,622,429 to Blank et al.; however, these modifications do not produce significant amounts of dialkyl- or trialkyl-substituted compounds. In fact, patentees only concern with dialkyl- or trialkyl-substituted compounds are in their inherent production within reactions of monoalkyl-substituted benzenes in these modified Gattermann-Koch processes. There is no teaching nor fair suggestion that any further modifications of patentees' procedures when utilized with di- or tri-substituted compounds would produce extremely high yields of the pure corresponding benzaldehydes. Furthermore, Blank et al.'s methods only produce, at the high end, yields up to 77% for monoalkyl-substituted benzaldehydes.

Another method for formylating alkylated benzenes has been disclosed within U.S. Pat. No. 4,195,040 to Renner. Such a teaching includes the formylation of di- and tri-alkylbenzenes; however, this reference also requires the presence and use of large amounts of gaseous hydrochloric acid. Such methods are thus highly undesirable since high levels of HCl are preferably avoided in industrial scale manufacturing, particularly when in gaseous form.

Another more recent method utilizes an HF-BF$_3$ medium in which to react substituted benzenes systems with carbon monoxide to formylate such compounds. This method has produced very good yields of the dialkyl-substituted benzaldehydes; however, the HF-BF$_3$ catalyst presents a significant safety hazard which ultimately adds to the cost of the final product.

Thus, there exists a need to develop a proper formylation reaction for substituted benzenes which produces high yields, does not require the utilization of large amounts of potentially dangerous HCl (or other acid) and other catalysts (and thus is relatively safe to perform), and is highly cost-effective. To date, the prior art has not accorded such an improved substituted benzene formylation procedure.

OBJECTS OF THE INVENTION

Therefore, an object of the invention is to provide a process for producing high yields of substituted benzaldehydes. A further object of the invention is to provide a highly cost-effective manner of producing such benzaldehydes which heretofore could not be produced in high yields without incurring potential problems from a safety perspective, particularly in a large-scale procedure. Another object of the invention is to provide a method of producing extremely pure substituted benzaldehydes thereby substantially reducing the need for subsequent distillation procedures. Additionally, it is an object of this invention to provide a method of producing specific substituted benzaldehydes which requires, if at all, only a very low amount of acid (such as aqueous HCl) in order to effectuate the necessary formylation procedure.

DETAILED DESCRIPTION OF THE INVENTION

Accordingly, this invention encompasses a method of producing a benzaldehyde of the formula (I)

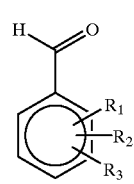

(I)

wherein $R^1$, $R^2$, and $R^3$ are the same or different and represent hydrogen or $C_1-C_4$ alkyl or any two of $R^1$, $R^2$, and $R^3$ may be fused together to form a cycloalkyl or cycloalkylene ring system; and wherein at most one of $R^1$, $R^2$, and $R^3$ is hydrogen; which method comprises contacting a substituted benzene of the formula (II)

(II)

wherein $R^1$, $R^2$, and $R^3$ are the same or different and represent hydrogen or $C_1-C_4$ alkyl or any two of $R^1$, $R^2$, and $R^3$ may be fused together to form a cycloalkyl or cycloalkylene ring system; and wherein at most one of $R^1$, $R^2$, and $R^3$ is hydrogen, in a carbon monoxide atmosphere having a pressure from about 20 to 200 psig, all in the presence of a metal halide, an acid selected from the group consisting of HCl, HBr, HF, HI, and mixtures thereof, and at least one solvent;

wherein the aqueous hydrochloric acid is present in a catalytic amount of from about 0.005 to about 0.01 moles per moles of the metal halide; and wherein the reaction temperature is from about −20° C. to about 25° C.

Any substituted benzene may be introduced within the inventive method. In particular, the reactant substituted benzene may be selected from the group consisting of $C_1-C_4$ dialkylbenzenes, $C_1-C_4$ trialkylbenzenes, tetralin, and indan. Specific compounds include, as merely examples o-xylene, p-xylene, m-xylene, p-diethylbenzene, o-diethylbenzene, m-diethylbenzene, 1, 2, 3-trimethylbenzene, 1, 2, 4-trimethylbenzene, 1, 2, 5-trimethylbenzene, 1, 3, 5-trimethylbenzene, tetralin, indan, or indene.

The metal halide is preferably aluminum chloride, although other such halides may be utilized, such as aluminum bromide, iron (III) chloride, copper (II) chloride, zinc chloride, zirconium chloride, zirconium bromide, and the like. Also, partially hydrated metal halides may be utilized as these may produce acid (such as hydrochloric acid) upon dissociation within the reaction vessel, thereby providing the necessary aqueous acid component (for instance $AlCl_3.XH_2O$, wherein X is at most 1, preferably lower than 0.5, and most preferably between 0.01 and 0.1). This dissociation actually produces the requisite small, catalytic amount of aqueous hydrochloric acid without having to introduce potentially hazardous aqueous hydrochloric acid into the reaction (although such an outside addition is also an available and preferred alternative). In the past variations of the Gattermann-Koch process, it was theorized that the metal halide reacted with hydrogen chloride and carbon monoxide (all in equivalent amounts) to produce a formyl cation complex which had the capability of attacking electrophilically the aromatic system. After washing with water, the metal halide was removed leaving the formylated benzene derivative. In this invention, hydrogen chloride is used, if at all, in only a minuscule catalytic amount (from about 0.005 to about 0.01 moles per mole of metal halide). The metal halide is preferably present in a stoichiometric molar ratio as compared with the substituted benzene from about 1:0.75 to about 1:6, preferably from 1:0.9 to about 1:3, and most preferably at a ratio of about 1:1. Without intending to be bound to any specific scientific theory, it is believed that such a small catalytic amount of acid (such as selected from the group consisting of HCl, HBr, HF, HI, and mixtures thereof) coupled with the metal halide produces a certain "driving amount" of the formyl cation complex. This "driving amount" thus appears to shut down the rate of possible side product formation (i.e., dimerization or polymerization, as merely examples) which have been found to occur upon utilization of standard and much larger amounts of HCl (gaseous, in particular) in past methods. Thus, it has been determined that this catalytic amount of aqueous HCl provides the necessary reaction which ultimately forms very pure high yields of the target di- and/or tri-alkyl benzaldehydes.

Furthermore, the utilization of hydrochloric acid is, surprisingly, highly critical to the ultimate formation of the desired substituted benzaldehydes. As noted above, it had been presumed that larger stoichiometric amounts of gaseous hydrogen chloride were necessary to form the electrophilically attacking formyl cation complex with the metal halide and the carbon monoxide as the actual reactant. It has now been found that gaseous HCl is unnecessary to produce the desired benzaldehyde (although the gaseous form is still possible in this inventive method). Also, it has been discovered that only very small catalytic amounts (as defined above) of (preferably) aqueous hydrochloric acid unexpectedly are required to form the beneficial formyl cation complex reactant in order to produce the desired substantially pure substituted benzaldehydes in high yields (although gaseous and dry forms of HCl also work). From a safety and convenience perspective, aqueous hydrochloric acid is the preferred form for this inventive method. Gaseous HCl poses a potential health hazard since control of such a gaseous state is rather difficult at times. Dry hydrochloric acid is more difficult to handle than the liquid form. Again, however, the hydrochloric acid may be added in any form, only preferably in aqueous solution.

As discussed above, it is important to note that this acid component (such as aqueous HCl) may either be charged into the overall reaction or may be generated simply upon dissociation of the metal halide in its hydrated form. Any molarity hydrochloric acid may be used, preferably the molarity is from about 0.01 to about 12, more preferably from about 10 to 12, and most preferably about 10 (concentrated), as long as the catalytic amount (in moles) in comparison to the metal halide is met and care is taken in handling such potentially corrosive material. Without the presence of hydrochloric acid (either aqueous, gaseous, or dry), the yield of substituted benzaldehyde is reduced; when too much hydrochloric acid is present, the reaction either generates different isomers, dimers, and/or polymers of the benzaldehyde (and thus reduces the yield and detrimentally reduces the purity of the final reaction product) or results in a reaction which produces a sludge-like solid. One further benefit to utilizing aqueous HCl with the metal halide (in particular aluminum chloride), is that, upon completion of the formylation reaction, the remaining aluminum chloride exhibits a relatively neutral pH level. Such a product cannot be used again in this process; however, such neutralized aluminum chloride can be resold for other uses (such as flocculants, anti-perspirant components, etc.). Such recycling and reuse of compounds thus provides an environmentally friendly procedure which reduces the amount of waste needed to be removed from the manufacturing locations.

The carbon monoxide is introduced at a pressure of between about 20 and 230 psig, preferably from about 50 to about 200 psig, and most preferably at a pressure of about 90 psig for a reaction with an alkyl-substituted benzene, and most preferably at a pressure of about 200 psig for a cycloalkyl-substituted benzene (i.e., tetralin). In the past, higher pressures (i.e., 200–600 psig) have been most readily utilized in such Gattermann-Koch modification reactions since it has been generally followed and understood that higher pressures result in faster reaction times (which, in turn, theoretically reduces costs in the long run). It has now been realized that the presence of alkyl groups on compounds which are subjected to high reaction pressures results in the production of various isomers, dimers, and the like, due to the highly reactive conditions such high pressures provide. Surprisingly, and counter to accepted practice, the inventive method of producing high yields of substantially pure substituted benzaldehydes requires a relatively low reaction pressure at which the carbon monoxide reactant is introduced within the reaction. Furthermore, lower pressures are highly desirable from a safety perspective (particularly with such potentially harmful compounds as carbon monoxide) and are much easier to handle within a large-scale manufacturing process. Standard, and thus readily available, reactors utilized in such large-scale manufacturing procedures are able to withstand pressures of at most 100 psi. Through the utilization of the low pressures associated with the preferred embodiment of the inventive method, costs can be reduced through the availability to utilize such standard reactors. Thus, the inventive method is cost efficient which translates into lower costs to the end user of the target substituted benzaldehydes.

It has also been found that the yield of the target substituted benzaldehyde compounds, when using, for example, aqueous HCl in catalytic amounts, is at its peak when the reaction temperature is optimized to about 0° C. (~95% yield of the target substituted benzaldehyde). A range of from about −10 to about 25° C., preferably from about −5 to about 5° C., and, again, most preferably about 0° C., should be followed. When the aqueous HCl is not added by hand (and thus is present due to the dissociation of the hydrated metal halide), the temperature must, surprisingly, be raised to about 25° C. in order to optimize the yield (again, about 70%). Since a higher temperature is expected to result in quicker reaction times, and thus possible higher yields, the necessity for utilizing a controlled system with a very low reaction temperature is very surprising, particularly since the yields have improved to levels unforeseen within modified Gattermann-Koch procedures. Furthermore, the utilization of such low temperatures is beneficial from both safety and cost perspectives. It is well known that the reactivity (and thus corrosiveness) of chlorides increases in relation to temperature, a reaction temperature of about 0° C., for example, will not corrode the reaction vessel at the same rate if a temperature of 50° C. or higher were followed (in fact, the higher temperature would theoretically result in a chloride being 32 times more reactive than the lower temperature listed above). Thus, with the utilization of low temperatures the manufacturing life-span of reaction vessels can be extended and the handling of the reactant materials is improved.

Also necessary within the inventive reactions is the presence of at least solvent other than the substituted benzene with which carbon monoxide will react to form the desired benzaldehyde in any proportion. Of particular necessity and thus preferred solvents (though not the exclusive solvents useful in this inventive process) are halogenated aromatic solvents, such as chlorotoluene, dichlorobenzene, and the like. Chlorotoluene is particularly preferred. Such solvents may be present in amounts as low as 0.1% of the total reaction composition or as high as about 99% (all by weight). Preferably, the solvent is added in an amount of from about 5 to about 50% by weight, more preferably from about 10 to about 40%, and most preferably from about 15 to about 25%. Such a solvent has proven beneficial in aiding in agitation during the reaction and in moderating the reactivity of the theorized cationic formyl catalyst within the inventive procedure. Thus, such a solvent allows for great versatility in formylating myriad different substituted benzenes. In particular, tetralin cannot be easily formylated without the utilization of such a solvent (or mixture of solvents). Thus, for this inventive method, a solvent must be present in order to properly effectuate the formylation of the target benzene and thus provide substantially pure benzaldehydes at high yields. Of course, by utilizing such solvents, subsequent distilling or azeotroping must be performed to separate the residual solvent from the target benzaldehyde. Thus, the utilization of only one solvent is highly preferred in the inventive method in order to reduce the costs and time involved in manufacturing the desired substituted benzaldehyde.

PREFERRED EMBODIMENTS OF THE INVENTION

Examples of the particularly preferred inventive methods are outlined below.

EXAMPLE 1

100.0 g of aluminum chloride (mol. wt. 133.34; 750 mmol) was poured over about 484.55 g of chlorotoluene in a 2 liter Paar®-brand stainless steel reaction vessel. Five drops of aqueous hydrochloric acid (concentrated) were then added and the vessel was sealed and purged two times with nitrogen at 60 psi. Then about 67.6 g of o-xylene (mol. wt. 106.17; 625 mmol) were charged to the vessel. The reactor was then purged three times with carbon monoxide at a pressure of about 110 psi. After the final purging, the vessel was vented and a final introduction of CO was made at a final pressure of about 110 psig, the pressure at which the reaction was maintained for the total reaction time of about 18 hours (the reaction temperature was maintained at about 5° C. for the duration as well). After that time, the resultant mixture (exhibiting a dark orange color) was purged three times with nitrogen and poured into about 570 g of ice water (which turned the solution a dark purple), to which was then added 500 mL of cyclohexane (which turned the color to grey and produced a two-phase mixture). The top, organic layer was removed and washed three times with water using a separatory funnel and dried over magnesium sulfate. The residual organic phase was then distilled under a vacuum to remove o-xylene, cyclohexane, and chlorotoluene, and left about 74.36 g of the 3,4-dimethylbenzaldehyde target product (554 mmol; yield of approximately 88.7%).

EXAMPLE 2

99.4 g of aluminum chloride (mol. wt. 133.34; 745 mmol) and about 74.0 g of o-xylene (mol. wt. 106.17; 697 mmol) were charged to a 2 liter Paar®-brand stainless steel reaction vessel with about 150 mL of o-dichlorobenzene. The vessel was sealed, purged two times with nitrogen at 50 psi, then once with carbon monoxide at a pressure of 100 psi. After the final purging, the vessel was vented and a final introduction of CO was made at a final pressure of about 40 psig, the pressure at which the reaction was maintained for the total reaction time of about 14 hours (the reaction temperature was maintained at about 18–200° C. for the duration as well). Once the reaction was complete, the resultant mixture was poured into about 600 g of ice water to produce about 900 mL of a two-phase mixture. The top, organic layer was removed and washed three times with water using a separatory funnel and dried over magnesium sulfate. The residual organic phase was then decolorized with activated charcoal and subsequently distilled under a vacuum to remove o-xylene (which has a boiling point of about 143–145° C.), then o-dichlorobenzene (which has a boiling point of from about 174 to 180° C.), and left about 50 g of the 3,4-dimethylbenzaldehyde target product (372.5 mmol; yield of approximately 50%).

EXAMPLE 3

102.4 g of aluminum chloride (mol. wt. 133.34; 770 mmol) and about 84.6 g of tetralin (mol. wt. 132.21; 640 mmol) were charged to a 2 liter Paar®-brand stainless steel reaction vessel with about 450 mL of chlorotoluene. Five drops of aqueous hydrochloric acid (concentrated) were then pipetted into the reaction vessel. The vessel was sealed, purged two times with nitrogen at 50 psi, then once with carbon monoxide at a pressure of 200 psi. After the final purging, the vessel was vented and a final introduction of CO was made at a final pressure of about 200 psig, the pressure at which the reaction was maintained for the total reaction time of about 14 hours (the reaction temperature was maintained at about −4 to 0° C. for the duration as well). After that time, the resultant mixture (exhibiting a dark orange color) was purged three times with nitrogen and poured into about 500 mL of ice water (which turned the solution a dark pink and eventually yellow upon the melting of the ice), to which was then added 500 mL of cyclohexane. The top, organic layer was removed and washed with water, KOH, and brine, all through the utilization of a separatory funnel and dried over magnesium sulfate. The residual organic phase was then distilled under a vacuum to remove tetralin, cyclohexane, and chlorotoluene, and left about 89.4 g of the tetralin aldehyde target product (560 mmol; yield of approximately 89.4%).

EXAMPLE 4 (Comparative)

200.27 g of aluminum chloride and about 994.87 g of tetralin were charged to a 2 liter Paar®-brand reaction vessel. Upon the addition of tetralin, the temperature of the mixture rose to about 60° C. due to the exothermic reaction between the two compounds. The vessel was sealed, purged three times with carbon monoxide with the pressure of the vessel increased to 90 psi for each purging. After the third time, the vessel was vented and a final introduction of CO was made at a pressure again of about 90 psi, the pressure at which the reaction was maintained for the duration of the reaction which lasted for about 18 hours (the reaction temperature was reduced to and maintained at about 25° C. for the duration as well). Once the reaction was complete, the reaction vessel (and resultant mixtures) was purged two times in a nitrogen atmosphere at 50 psi. The recovered product mixture (a red/yellow material) appeared as an emulsion. This material was then quenched, washed with about 500 mL of ice water, and vacuum distilled. Upon distillation, tetralin (from about 83 to about 85° C. at 15 mm Hg), the red/yellow material (about 150° C. at 15 mm Hg), and two other unknown fractions (the first at about 220–225° C. and the other at about 255° C. at 15 mmHg) were recovered. None of these materials were the target tetralin benzaldehyde.

Having described the invention in detail it is obvious that one skilled in the art will be able to make variations and modifications thereto without departing from the scope of the present invention. Accordingly, the scope of the present invention should be determined only by the claims appended hereto.

That which is claimed is:

1. A method of producing a benzaldehyde of the formula (I)

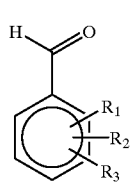

wherein $R^1$, $R^2$, and $R^3$ are the same or different and represent hydrogen or $C_1$–$C_4$ alkyl or any two of $R^1$, $R^2$, and $R^3$ may be fused together to form a cycloalkyl ring system; and which method comprises the reaction between a substituted benzene of the formula (II)

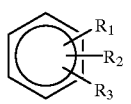

wherein $R^1$, $R^2$, and $R^3$ are the same or different and represent hydrogen or $C_1$–$C_4$ alkyl or any two of $R^1$, $R^2$, and $R^3$ may be fused together to form a cycloalkyl ring system; and wherein at most one of $R^1$, $R^2$, and $R^3$ is hydrogen, and a carbon monoxide atmosphere having a pressure from about 20 to 230 psig, in the presence of a metal halide, an acid selected from the group consisting of HCl, HBr, HF, HI, and mixtures thereof, and at least one solvent other than a substituted benzene of the formula (II);

wherein the acid is present in a catalytic amount of from about 0.0001 to about 0.01 moles per moles of the metal halide; and wherein the reaction temperature is from about −20° C. to about 25° C.

2. The method of claim 1 wherein
said acid is hydrochloric acid.

3. The method of claim 2 wherein
said hydrochloric acid is present in aqueous solution.

4. The method of claim 1 wherein
said metal halide is selected from the group consisting of aluminum chloride, aluminum bromide, zirconium chloride, and any mixtures thereof.

5. The method of claim 2 wherein
said temperature is from about −10° to about 5° C. and said hydrochloric acid is added to the reaction.

6. The method of claim 2 wherein
said hydrochloric acid is added to the reaction.

7. The method of claim 2 wherein
said hydrochloric acid is generated within the reaction.

8. The method of claim 3 wherein
said hydrochloric acid is added to the reaction.

9. The method of claim 3 wherein
said hydrochloric acid is generated within the reaction.

10. The method of claim 2 wherein
said temperature is about 0° C. and said metal halide is aluminum chloride.

11. The method of claim 3 wherein
said temperature is about 0° C. and said metal halide is aluminum chloride.

12. The method of claim 1 wherein
said substituted benzene of Formula (II) is selected from the group consisting of o-xylene, p-xylene, m-xylene, p-diethylbenzene, o-diethylbenzene, m-diethylbenzene, 1, 2, 3-trimethylbenzene, 1, 2, 4-trimethylbenzene, 1, 2, 5-trimethylbenzene, and 1, 3, 5-trimethylbenzene, tetralin, indan, and indene.

13. The method of claim 2 wherein
said substituted benzene of Formula (II) is selected from the group consisting of o-xylene, p-xylene, m-xylene, p-diethylbenzene, o-diethylbenzene, m-diethylbenzene, 1, 2, 3-trimethylbenzene, 1, 2, 4-trimethylbenzene, 1, 2, 5-trimethylbenzene, and 1, 3, 5-trimethylbenzene, tetralin, indan, and indene.

14. The method of claim 10 wherein
said substituted benzene of Formula (II) is selected from the group consisting of o-xylene, p-xylene, m-xylene, p-diethylbenzene, o-diethylbenzene, m-diethylbenzene, 1, 2, 3-trimethylbenzene, 1, 2, 4-trimethylbenzene, 1, 2, 5-trimethylbenzene, and 1, 3, 5-trimethylbenzene, tetralin, indan, and indene.

15. The method of claim 11 wherein
said substituted benzene of Formula (II) is selected from the group consisting of o-xylene, p-xylene, m-xylene, p-diethylbenzene, o-diethylbenzene, m-diethylbenzene, 1, 2, 3-trimethylbenzene, 1, 2, 4-trimethylbenzene, 1, 2, 5-trimethylbenzene, and 1, 3, 5-trimethylbenzene, tetralin, indan, and indene.

* * * * *